United States Patent
Pendell-Jones et al.

(10) Patent No.: US 7,359,040 B1
(45) Date of Patent: Apr. 15, 2008

(54) SIMULTANEOUS CAPTURE OF FLUORESCENCE SIGNATURE AND RAMAN SIGNATURE FOR SPECTROSCOPY ANALYSIS

(75) Inventors: James E. Pendell-Jones, Baltimore, MD (US); Ryan E. Da Re, Bristow, VA (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 8 days.

(21) Appl. No.: 11/580,051

(22) Filed: Oct. 13, 2006

(51) Int. Cl.
*G01N 21/64* (2006.01)
*G01N 21/65* (2006.01)

(52) U.S. Cl. .................. 356/73; 356/301; 356/318; 250/461.1

(58) Field of Classification Search ............ 356/72, 356/73, 301
See application file for complete search history.

(56) References Cited

U.S. PATENT DOCUMENTS

| | | | |
|---|---|---|---|
| 3,850,525 A * | 11/1974 | Kaye ..................... 356/301 |
| 4,689,052 A | 8/1987 | Ogren et al. |
| 5,835,649 A | 11/1998 | Turner et al. |
| 6,287,869 B1 | 9/2001 | Hug et al. |
| 6,693,944 B1 | 2/2004 | Hug et al. |
| 7,113,275 B2 | 9/2006 | Gardner, Jr. et al. |
| 7,245,371 B2 * | 7/2007 | Wang et al. ............ 356/301 |
| 2002/0109110 A1 * | 8/2002 | Some et al. ............ 250/559.4 |
| 2006/0061762 A1 | 3/2006 | Dwight et al. |

OTHER PUBLICATIONS

R. Bombach, W. Hubschmid, A. Inauen, B. Kappeli, "Simultaneous Raman and LIF Measurements in a Catalytic Burner," Proceedings 22nd IEA Task Leaders Meeting 2000 on Energy Conservation and Emissions.

S. Hong, J. Birmingham, M. Fountain, "Mesochannel Gas Sampler for Rapid Sample Collection and Concentration, " Mar. 2001, pp. 1-15, Prepared for the Department of Energy Under DOE Grant No. DE-FG03-00ER83048 by MesoSystems Technology, Inc. Kennewich, Washington.

Lockheed Martin Maritime Systems & Sensors, "Biological Aerosol Warning System," Cleared for Public Domain Releease DoD/00-S-0607, 12/99, Aug. 2003, Manassas, VA.

General Dynamics Armament and Technical Products, "Biological Agent Warning Sensor," 2007, Charlotte, NC.

* cited by examiner

*Primary Examiner*—F. L. Evans
(74) *Attorney, Agent, or Firm*—Edell, Shapiro & Finnan, LLC

(57) ABSTRACT

A system and method are provided for analyzing a substance using spectroscopy techniques. Raman scattered energy and fluorescence scattered energy are simultaneously excited in the substance from a beam of ultraviolet light. The Raman scattered energy and the fluorescence scattered energy, as well as the fluorescence energy lifetime are detected and analyzed to characterize or identify the substance.

19 Claims, 3 Drawing Sheets

US 7,359,040 B1

SIMULTANEOUS CAPTURE OF FLUORESCENCE SIGNATURE AND RAMAN SIGNATURE FOR SPECTROSCOPY ANALYSIS

BACKGROUND OF THE INVENTION

The present invention relates to devices, systems and methods for remotely detecting hazardous substances of a chemical or biological nature.

Spectroscopy is a useful technology for characterizing and/or identifying substances by analyzing the substance's response to application of certain types of light. One type of response that is useful is Raman scattering. Raman spectroscopy is a spectroscopic technique used to study vibrational, rotational, and other low-frequency modes in a system.

Fluorescence is another response useful to discern characteristics of a substance. Fluorescence refers to emission of light caused when a material absorbs optical energy of one wavelength and re-emits light of another wavelength. Fluorescence spectroscopy has evolved into a powerful tool for the study of chemical, semiconductor, photochemical, and biochemical species. Fluorescence lifetime is the average time that a molecule spends in the excited state before emitting a photon and returning to the ground state. Fluorescence lifetime is also an important and unique feature of an excited state.

It is desirable to provide a spectroscopy system and method that uses both Raman scattered energy and fluorescence scattered energy produced simultaneously in response to a beam of light in order to evaluate (characterize and/or identify) a substance.

SUMMARY OF THE INVENTION

Briefly, a system and method are provided for analyzing a substance using spectroscopy techniques. Raman scattered energy and fluorescence scattered energy are simultaneously excited in the substance from a beam of ultraviolet light. The Raman scattered energy and the fluorescence scattered energy are detected and analyzed to characterize or identify the substance.

DETAILED DESCRIPTION

Figure 1:
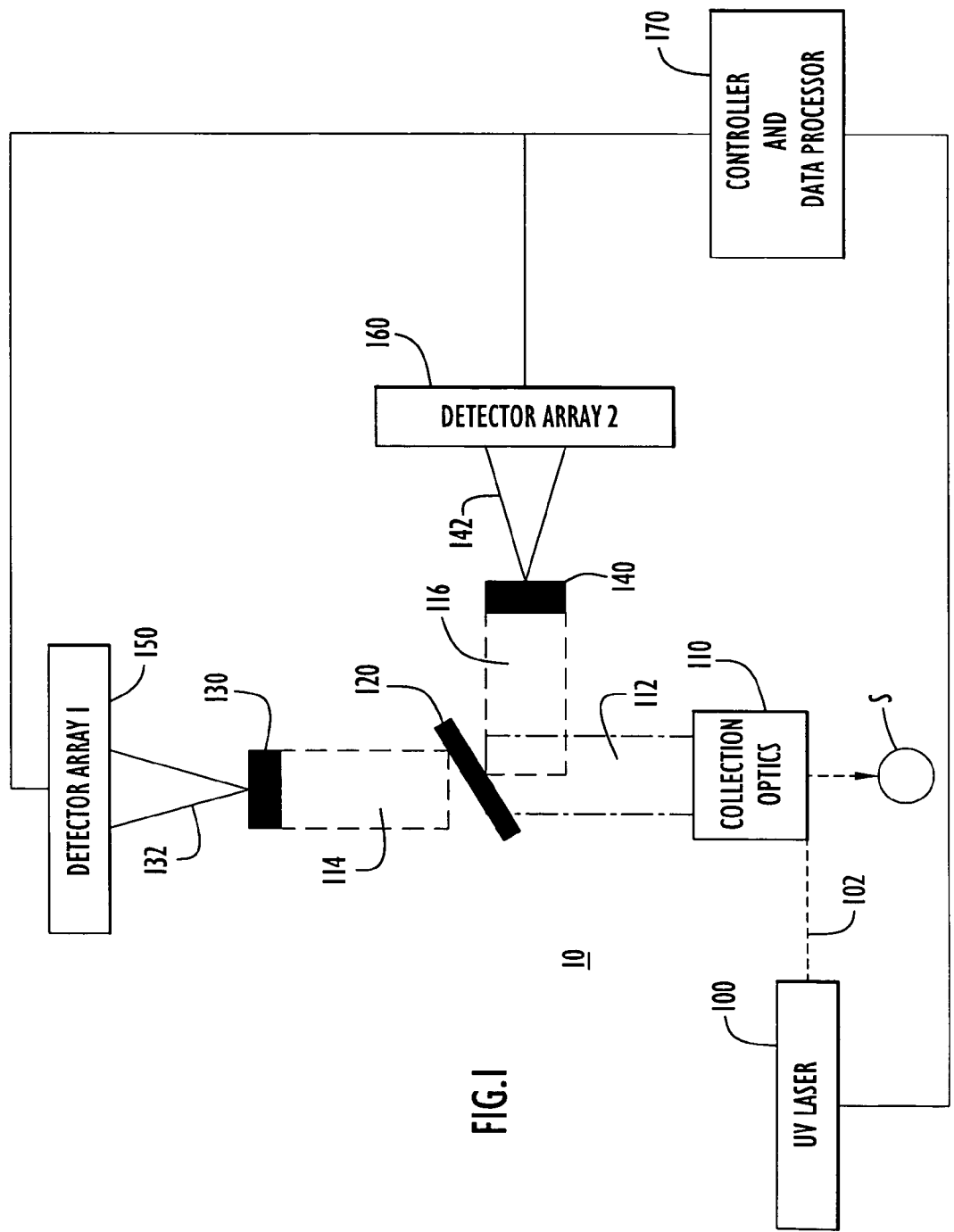
FIG. 1 is a block diagram of a system according to an embodiment of the invention.

Referring first to FIG. 1, a spectroscopy analysis system is shown at reference numeral 10 for simultaneously capturing Raman scattering and fluorescence scattering of a sample substance for analysis according to an embodiment of the invention. The spectroscopy analysis system 10 comprises an ultraviolet light source 100, collection optics 110, a wavelength selective optical element 120, a first dispersing element 130, a second dispersing element 140, a first detector 150 and a second detector 160. A controller and data processor 170 is provided that controls the light source 100 and analyzes the data produced by the first and second detectors 150 and 160.

The light source 100 is an ultraviolet light source that is capable of producing a beam of ultraviolet light in order to simultaneously excite Raman scattering and fluorescence scattering from the substance, where the Raman scattering and fluorescence scattering occur in different wavelength regions. For example, the light source 100 is a "deep" ultraviolet (UV) excitation source (e.g., less than 263 nm) and may take the form of an excimer, alexandrite, Nd:YLF, or Nd:YAG laser. Again, UV light in this wavelength region can simultaneously excite Raman or Resonance Raman, and fluorescence scattering over separate wavelength regions.

The light beam from the light source 100 is shown at reference numeral 102 and is directed (through one or more optical elements not shown for simplicity) to a surface on which a substance S to be analyzed resides. The types of substances that may be characterized or identified using the techniques described herein include, without limitation, solid or liquids, including airborne aerosol particles, of a chemical or biological origin, as well as flowing solutions, pharmaceutical crystals, meteorites, etc.

The collection optics 110 captures the scattered optical energy and separates out the Raman and fluorescence scattered energy from Raleigh scattered energy. For example, the collection optics comprises a telescope or other optical element for focusing the scattered optical energy.

The collection optics 110 focuses the scattered optical energy shown at reference numeral 112 to the wavelength selective optical element 120. The wavelength selective optical element 120 separates the Raman scattered energy from the fluorescence scattered energy since they are in two different wavelength regions. By way of example only, the wavelength selective optical element 120 is a dichroic mirror, tunable bandpass filter or reflective Kerr medium capable of directing Raman scattered energy 114 in a first wavelength region to a first light dispersing element 130 and directing fluorescence scattered energy 116 in a second wavelength region to a second light dispersing element 140. For example, the Raman scattered energy 114 is in a first wavelength region extending from approximately 265 nm to 285 nm and the fluorescence scattered energy is in a second wavelength region extending from approximately 290 nm to 550 nm if excited with 262 nm monochromatic light. In one embodiment, the fluorescence scattered energy 116 is directed by reflection from the wavelength selective optical element 120 to the second light dispersing element 140 while the Raman scattered energy 114 passes through the wavelength selective optical element 120 to the first light dispersing element 130.

The first and second light dispersing elements 130 and 140 may be, for example, diffraction gratings or prisms, or high and low pass filter combinations that serially split light into discrete wavelength bands. The first light dispersing element 130 diffracts or otherwise disperses the Raman scattered energy 114 to separate out the constituent wavelengths (colors) that make up a Raman scattering 132 and directs these constituent wavelengths to the first detector 150. The second light dispersing element diffracts or otherwise disperses the fluorescence scattered energy 116 to separate out the constituent wavelengths that make up the fluorescence scattering 142 and directs these constituent wavelengths to the second detector 160.

The first detector 150 detects the light intensity at each of a plurality of wavelength "bins" and produces a signal or digital data that represents the Raman scattering. Similarly, the second detector detects the light intensity at each of a plurality of wavelength bins and produced a signal or digital data that represents the fluorescence scattering. By way of example, the first detector 150 may be a gated detector array such as an optical intensified charged coupled device (ICCD) that converts the incoming scattered energy to digital data. Similarly, the second detector 160 is an ICCD, or an array of very fast gated photodiodes that can capture not only the shape of the fluorescence scattering but also the snapshots of the fluorescence scattering at multiple time instances over a time interval following a pulse or burst of the UV light beam for purposes of deriving the fluorescence lifetime at each of the plurality of wavelength bins, or any subset of available wavelength bins.

The data produced by the first detector 150 and the second detector 160 is coupled to the controller and data processor 170. The controller and data processor 170 controls the actuation timing of the light source 100 and also analyzes the Raman data and fluorescence data produced by the first and second detectors 150 and 160, respectively.

Figure 2:
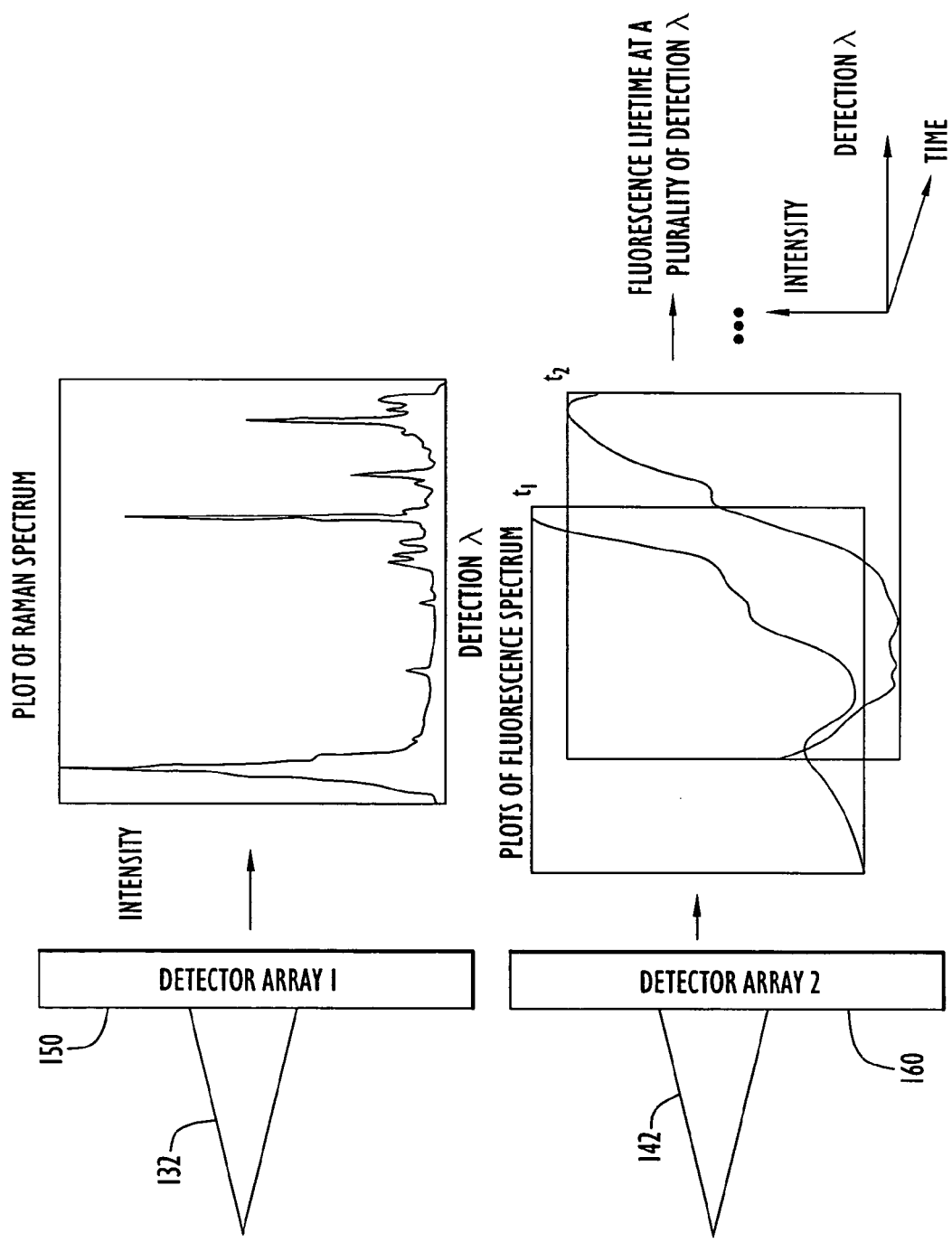
FIG. 2 is a block diagram of the system and illustrating exemplary Raman data and fluorescence data according to an embodiment of the invention.
Figure 3:
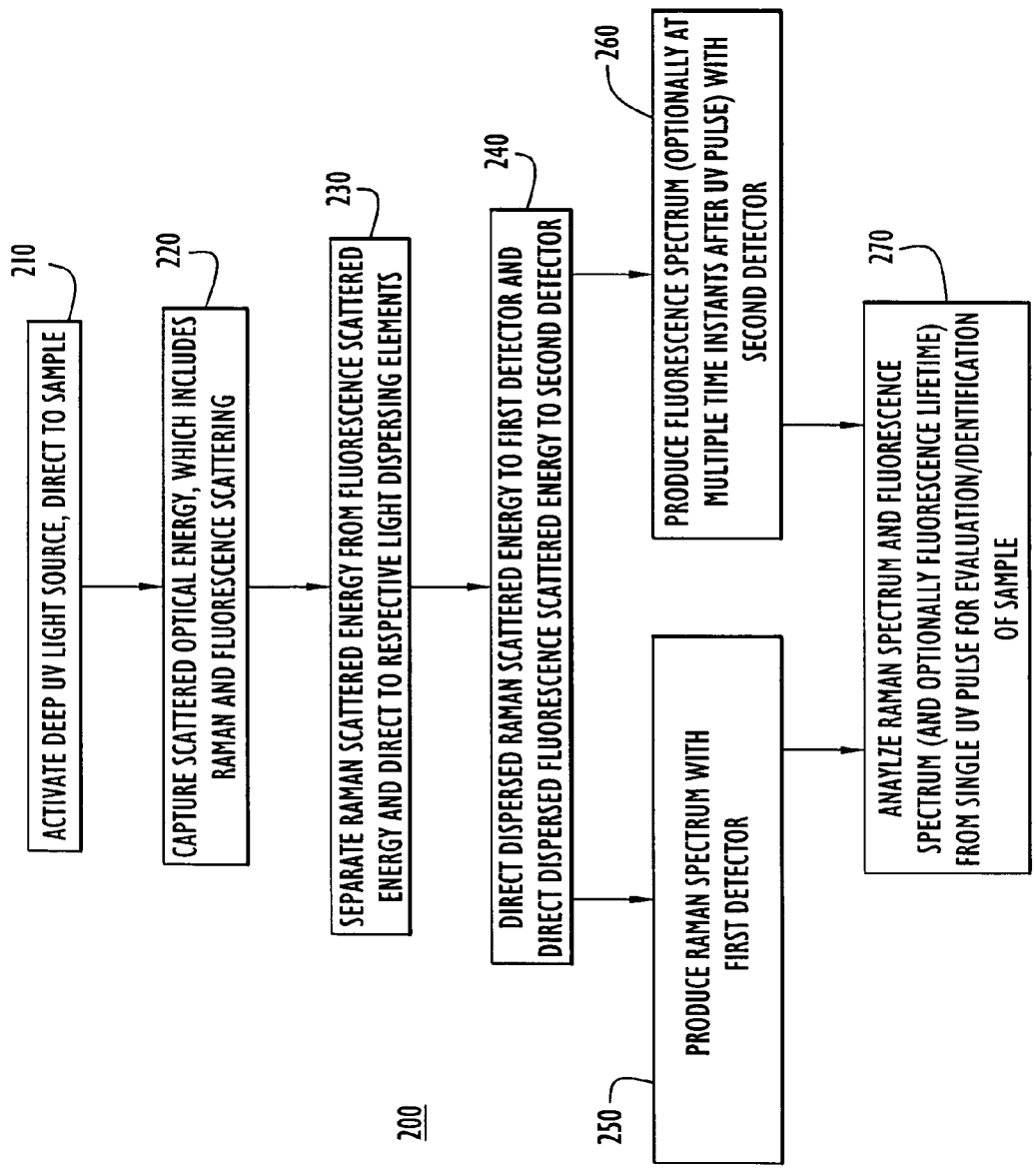
FIG. 3 is a flow chart depicting a method for spectroscopy analysis according to an embodiment of the invention.

Reference is now made to FIGS. 2 and 3, with continued reference to FIG. 1, for a description of an operation of the system 10. FIG. 2 illustrates plots of exemplary Raman data and fluorescence data. FIG. 3 illustrates a flow chart depicting a method 200 corresponding to operation of the system 10 according to an embodiment of the invention. At 210, the light source 100 is activated to send a deep UV light beam to a sample on a surface. For example, the light source may produce a beam of light in a wavelength region below or less than 263 nm. The UV light interacts with the substance and excites scattered optical energy including Raman scattered energy and fluorescence scattered energy. At 220, the scattered optical energy is captured by the collection optics 110. At 230, the selective wavelength optical element 120 separates the Raman scattered energy from the fluorescence scattered energy and directs the Raman scattered energy to the first light dispersing element 130 and directs the fluorescence scattered energy (that is in a different wavelength region than the Raman scattered energy) to the second light dispersing element 140.

At 240, the first light dispersing element 130 disperses the Raman scattered energy and directs the constituent wavelengths of the Raman scattered energy to the first detector 150. Similarly, the second light dispersing element 140 disperses fluorescence scattered energy is directed to the second detector 160. At 250, the first detector 150 produces data representing the constituent wavelengths that make up the Raman photons and substantially simultaneously at 260 the second detector 160 produces data representing the constituent wavelengths that make up the fluorescence photons. In one embodiment, the fluorescence scattering is produced at 260 by the second detector 160 at each of a plurality of time instances shown as $t_1, t_2, \ldots$, over a time interval after application of a pulse or burst of light from the light source 100 at 210. The Raman data and the fluorescence data is coupled to the controller and data processor 170. In one embodiment, the controller and data processor 170 further computes fluorescence lifetime data at one or more detection wavelengths from fluorescence data obtained from the second detector 140 at each of the plurality of time instances (hereinafter referred to as the "fluorescence samples") over the time interval following the UV light beam pulse or burst. Thus, the Raman data may comprise two dimensions of data, and FIG. 2 shows exemplary data plotted with intensity on the y-axis and detection wavelength (channel) on the x-axis. The fluorescence data may comprise three dimensions of data and FIG. 2 shows exemplary data plotted with intensity on the y-axis, detection wavelength (channel) on the x-axis and time on the z-axis. The controller and data processor 170 may average the Raman data (and/or fluorescence data) over several pulses in order to increase the signal-to-noise ratio, or to improve sensitivity in high clutter environments.

At 270, the controller and data processor 170 analyzes the Raman data and fluorescence data to characterize or identify the sample substance by comparing the Raman data against a Raman spectra library of known substances and comparing the fluorescence data against a fluorescence spectral library of known substances. Alternatively, at 270, the controller and data processor 170 analyzes the Raman data, fluorescence data and fluorescence lifetime data (at one or more wavelengths) against a library of fluorescence lifetime data to characterize or identify the sample substance.

An advantage of the system and method according to the embodiments of the present invention is that the UV laser-induced fluorescence spectral profile of target substances (chemicals and/or biological) can be correlated with the Raman spectral profile because the Raman spectral profile and fluorescence spectral profile are collected simultaneously from one source. Furthermore, the light source 100 may be a pulsed laser that provides sufficiently fast pulse widths (picoseconds) to simultaneously produce a Raman spectral profile, a fluorescence spectral profile, and fluorescence lifetime (from multiple fluorescence samples) relative to the excitation laser timing profile.

The system and methods described herein may be embodied in other specific forms without departing from the spirit or essential characteristics thereof. The foregoing embodiments are therefore to be considered in all respects illustrative and not meant to be limiting.

What is claimed is:

1. A method for analyzing a substance comprising:
   a. directing a beam of ultraviolet light onto the substance to substantially simultaneously excite Raman scattering and fluorescence scattering from the substance, wherein the Raman scattering and fluorescence scattering occur in different wavelength regions;
   b. capturing scattered optical energy from the substance, wherein the scattered optical energy includes Raman scattered energy and fluorescence scattered energy;
   c. separating the Raman scattered energy and the fluorescence scattered energy in the captured optical energy;
   d. generating Raman data from the Raman scattered energy and generating fluorescence data from the fluorescence scattered energy; and
   e. generating fluorescence lifetime data at one or more wavelengths from the fluorescence data produced over a time interval following a pulse or burst of the beam of ultraviolet light.

2. The method of claim 1, wherein (a) directing comprises directing a single pulse or burst of the beam of ultraviolet light, and wherein said (b) capturing, (c) separating, and (d) generating and (e) generating are performed based on said single pulse.

3. The method of claim 1, and further comprising analyzing the Raman data, the fluorescence data and the fluorescence lifetime data to characterize or identify the substance.

4. The method of claim 1, and further comprising computing an average of the Raman data and/or fluorescence data obtain from several pulses of the beam of ultraviolet light.

5. The method of claim 1, and further comprising analyzing the Raman data and the fluorescence data to characterize or identify the substance.

6. The method of claim 1, wherein (a) directing comprises directing a beam of light whose wavelength is less than approximately 263 nm.

7. A spectroscopy analysis system, comprising:
a. an ultraviolet light source that produces a beam of ultraviolet light directed at a substance in order to substantially simultaneously excite Raman scattering and fluorescence scattering from the substance, wherein the Raman scattering and fluorescence scattering occur in different wavelength regions;
b. at least one optical collecting element that collects scattered optical energy that includes Raman scattered energy and fluorescence scattered energy;
c. an optical wavelength selective element that separates the Raman scattered energy and the fluorescence scattered energy from the scattered optical energy;
d. a first light dispersing element that receives and disperses the Raman scattered energy into constituent wavelengths of light;
e. a first detector that receives the wavelengths of light produced by the first light dispersing element and produces Raman data;
f. a second light dispersing element that receives and disperses the fluorescence scattered energy into constituent wavelengths of light; and
g. a second detector that receives the wavelengths of light produced by the second light dispersing element and produces fluorescence data.

8. The system of claim 7, and further comprising a data processor that is coupled to the first and second detectors and analyzes the Raman data and the fluorescence data to characterize or identify the substance.

9. The system of claim 8, wherein the data processor generates fluorescence lifetime data at one or more wavelengths from fluorescence data produced by said second detector over a time interval following a pulse or burst of said beam of ultraviolet light.

10. The system of claim 9, wherein said data processor analyzes the Raman data, fluorescence data and fluorescence lifetime data to characterize or identify the substance.

11. The system of claim 7, wherein said data processor analyzes the Raman data and fluorescence data to characterize or identify the substance.

12. The system of claim 7, wherein said ultraviolet light source generates a beam of light in a wavelength region less than 263 nm.

13. A spectroscopy analysis system, comprising:
a. means for producing a beam of ultraviolet light directed at a substance in order to simultaneously excite Raman scattering and fluorescence scattering from the substance, wherein the Raman scattering and fluorescence scattering occur in different wavelength regions;
b. means for separating Raman scattered energy and fluorescence scattered energy from optical energy scattered by the substance;
c. first means for producing Raman data from the Raman scattered energy;
d. second means for producing fluorescence data the fluorescence scattered energy; and
e. means for analyzing the Raman data and the fluorescence data to characterize or identify the substance, wherein said means for analyzing further generates fluorescence lifetime data at one or more wavelengths from the fluorescence data produced over a time interval following a pulse or burst of the beam of ultraviolet light.

14. The system of claim 13, wherein said means for analyzing correlates the Raman data, fluorescence data and fluorescence lifetime data to characterize or identify the substance.

15. The system of claim 13, wherein said means for analyzing analyzes the Raman data and fluorescence data to characterize or identify the substance.

16. A method for analyzing a substance using spectroscopy techniques comprising:
detecting Raman scattered energy and fluorescence scattered energy simultaneously excited in the substance from a beam of ultraviolet light;
capturing scattered optical energy from the substance, wherein the scattered optical energy includes the Raman scattered energy and the fluorescence scattered energy;
separating the Raman scattered energy and the fluorescence scattered energy in the captured optical energy;
generating Raman data from the constituent wavelengths produced by dispersing the Raman scattered energy and generating fluorescence data from the constituent wavelengths produced by dispersing the fluorescence scattered energy;
deriving fluorescence lifetime data from fluorescence data obtained at a plurality of time instances over a time interval; and
analyzing the Raman data, the fluorescence data and fluorescence lifetime data to characterize or identify the substance.

17. The method of claim 16, and further comprising dispersing the Raman scattered energy into its constituent wavelengths and dispersing the fluorescence scattered energy into its constituent wavelengths.

18. The method of claim 16, wherein analyzing comprises correlating the Raman data, fluorescence data and fluorescence lifetime data to characterize or identify the substance.

19. The method of claim 16, and further comprising averaging the Raman data and/or fluorescence data obtained from several pulses of the beam of ultraviolet light.

* * * * *